(12) United States Patent
Liu

(10) Patent No.: US 6,172,510 B1
(45) Date of Patent: Jan. 9, 2001

(54) SYSTEM FOR DETECTION OF FLAWS BY USE OF MICROWAVE RADIATION

(75) Inventor: John M. Liu, Columbia, MD (US)

(73) Assignee: The United Sates of America as represented by the Secretary of the Navy, Washington, DC (US)

( * ) Notice: Under 35 U.S.C. 154(b), the term of this patent shall be extended for 0 days.

(21) Appl. No.: 09/223,031

(22) Filed: Dec. 30, 1998

(51) Int. Cl.⁷ .................................................. G01N 22/04
(52) U.S. Cl. ............................................ 324/632; 324/642
(58) Field of Search ................................. 324/632, 642, 324/644, 639, 534, 631, 337

(56) References Cited

U.S. PATENT DOCUMENTS

| | | |
|---|---|---|
| 3,144,601 | 8/1964 | Slabodsky . |
| 3,233,172 | 2/1966 | Luoma . |
| 3,549,986 | 12/1970 | Prine . |
| 3,562,642 | 2/1971 | Hochschild . |
| 3,651,395 * | 3/1972 | Owen et al. .......................... 324/337 |
| 3,810,005 | 5/1974 | Bennion et al. . |
| 4,097,796 | 6/1978 | Lunden . |
| 4,234,844 * | 11/1980 | Yuki ...................................... 324/642 |
| 4,344,030 | 8/1982 | Anderson et al. . |
| 4,500,835 | 2/1985 | Heikkila . |
| 4,514,680 | 4/1985 | Heikkila et al. . |
| 4,707,652 | 11/1987 | Lowitz . |
| 5,068,614 | 11/1991 | Fields et al. . |
| 5,128,621 * | 7/1992 | Berthaud et al. ..................... 324/639 |
| 5,363,050 | 11/1994 | Guo et al. . |
| 5,440,238 | 8/1995 | Martens et al. . |
| 5,497,100 | 3/1996 | Reiser et al. . |
| 5,502,394 | 3/1996 | Piau . |
| 5,565,628 * | 10/1996 | Lorraine ................................ 73/642 |
| 5,859,535 * | 1/1999 | Liu ...................................... 324/632 |

* cited by examiner

Primary Examiner—Safet Metjahic
Assistant Examiner—Vincent Q. Nguyen
(74) Attorney, Agent, or Firm—John Forrest; Jacob Shuster

(57) ABSTRACT

Targeted portions of material layered structure is probed by microwave radiation focussed onto the targeted portion by adjustment of antenna position and orientation establishing a single oblique incidence path for reflection of antenna emitted probing radiation. Signal measurements of the radiation along the oblique incidence path is obtained to provide for evaluation and detection of defects in the targeted portion of the structure being probed.

8 Claims, 4 Drawing Sheets

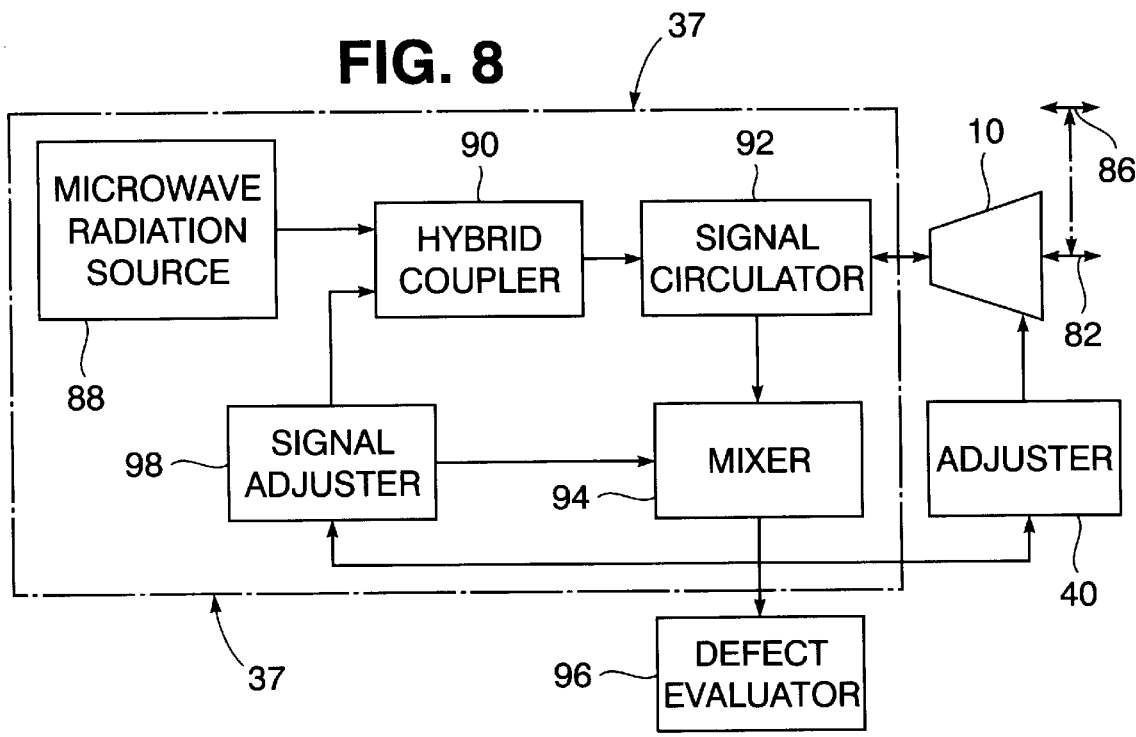

US 6,172,510 B1

SYSTEM FOR DETECTION OF FLAWS BY USE OF MICROWAVE RADIATION

The present invention relates generally to non-destructive evaluation of defects within structural materials by use of microwave radiation, one example of which is set forth in prior copending application Ser. No. 08/798,683 now U.S. Pat. No. 5,859,535 filed Feb. 12, 1997, now U.S. Pat. No. 5,859,535 the disclosure of which is incorporated herein by reference and with respect to which the present application is a continuation-in-part.

BACKGROUND OF THE INVENTION

The detection and evaluation of structural flaws by non-destructive use of radiation is generally known in the art, including use of microwave radiation exhibiting certain advantages over other forms of radiation such as x-ray, ultrasound and thermography radiation. Such uses of microwave radiation include emission and reflection of the radiation after interaction with the targeted material for detecting the presence or absence of a defect therein. Microwave radiation types of defect detection systems heretofore involved one or more antennas for emission of the radiation and reception of reflective radiation. Some of the advantages over the use of other forms of radiation include, avoiding use of a couplant and heat diffusion means, increasing depth of detection and avoiding the provision of radiation hazard prevention. It is therefore an important object of the present invention to enlarge evaluation of structural flaws by the advantageous use of microwave radiation as disclosed in connection with the embodiment covered in the aforementioned prior copending parent application, Ser. No. 08/798,683 now U.S. Pat. No. 5,859,535. According to the disclosure in such prior copending parent application, detection location and sizing of an internal defect in a thick non-metallic material or composite is achieved by isolating in time reflections of microwave radiation from external surfaces using Fourier transformation of frequency domain data applied in a straight forward manner.

SUMMARY OF THE INVENTION

In accordance with the present invention, microwave radiation is both transmitted from and received by one antenna positioned and orientated to transmit and receive microwave energy along an oblique angle from the surface normal of a targeted material at a focus location from which reflected radiation originates in order to identify and evaluate defects from measurement of the microwave radiation. Evaluation of structural flaws is thereby achieved through calculations based on readings of radiation measurement data with respect to a single radiation path, pursuant to techniques constituting an extension of the approach set forth in the aforementioned prior copending parent application, wherein reflection from a defect is not completely separated in time with respect to reflection originating from some interfaces in the material structure being targeted. By use of gating techniques, generally known in the art, the data on reflections from boundaries or interfaces are excluded from data on reflections originating from targeted defects of interest in accordance with the present invention. The new approach or technique of the present invention involves utilization of frequency domain response from either an internal thin layer or an external surface of the targeted structure after a reverse Fourier transformation is applied to the time domain for return of gated reflection to the frequency domain. Such new technique is based on the defect induced changes in the resonances of the material layer in question in the frequency domain. This new approach is also applicable to cases wherein the signals originated from material interfaces near the defect are not completely excluded from the defect signal by time gating.

BRIEF DESCRIPTION OF DRAWING FIGURES

A more complete appreciation of the invention and many of its attendant advantages will be readily appreciated as the same becomes better understood by reference to the following detailed description when considered in connection with the accompanying drawing wherein:

FIG. 8 is a block diagram depicting a reflectometric system for detection of defects in structural arrangements as shown in FIGS. 7A, 7B, 7C and 7D.

DETAILED DESCRIPTION OF PREFERRED EMBODIMENTS

Figure 1:
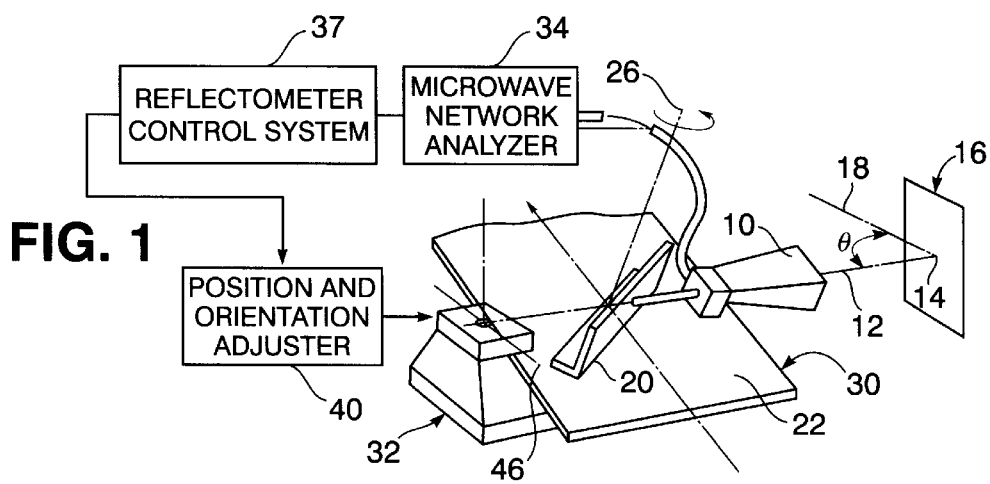
FIG. 1 is a simplified perspective view of an antenna arrangement in accordance with the present invention for emission and reception of microwave radiation focused on targeted material, together with a block diagram of a defect detection and evaluation system associated therewith.

Referring now to the drawing in detail, one embodiment of the invention is illustrated in FIG. 1 which depicts a single antenna 10 from which a microwave radiation beam is emitted along a normal surface incidence path 12 toward a focus location 14 in a non-metallic type of target 16 involving for example dielectric materials or composites. Such outgoing microwave radiation from antenna 10 focused onto the target 16 is reflected from the target surface spaced by a stand-off distance from the antenna 10 along the path 12. When disposed in another position and at a different angular orientation relative to the target 16, the antenna 10 emits or receives radiation along another path 18 at an oblique angle (θ) to the path 12 as denoted in FIG. 1.

Also depicted by way of example in FIG. 1, is a support arrangement for the antenna 10 so as to accommodate its repositioning and reorientation on a platform 30 for establishment of the different radiation paths 12 and 18. An optical beam splitter 20 shown in FIG. 1 is angularly reoriented about a bearing axis 26 on scattering surface plane 22 of the platform 30, which is supported for angular adjustment about the incidence path 12 on a suitable fixed stand 32. As diagrammed in FIGS. 2A and 2B, the platform 30 also supports an optical mirror 24 which is utilized in cooperation with the beam splitter 20 in a manner generally known in the art to angularly adjust the antenna 10 on the platform 30 along a translation path 28 to establish the radiation path 18 focused on the same target location 14 at the oblique angle (θ) to path 12.

FIG. 1 also diagrams an operative connection of the antenna 10 to a calibrated microwave network analyzer 34 which is per se known in the art. Such a microwave network analyzer 34 includes for example a wide frequency band microwave energy source, multi-frequency transmitter and coherent receiver from which signal measurement data is received and coupling circuits through which the transmitter and receiver are operatively connected to the antenna 10. A signal separation means is also included for independently processing outgoing and returned scattering signals. Pursuant to the present invention, the processed signal measurement data from the analyzer 34 undergoes signal processing in a reflectometer control system 37 through which control data is generated and fed to an adjuster 40 for adjustment of position and orientation of the antenna 10 on the scattering plane 22 as aforementioned.

Figure 2A:
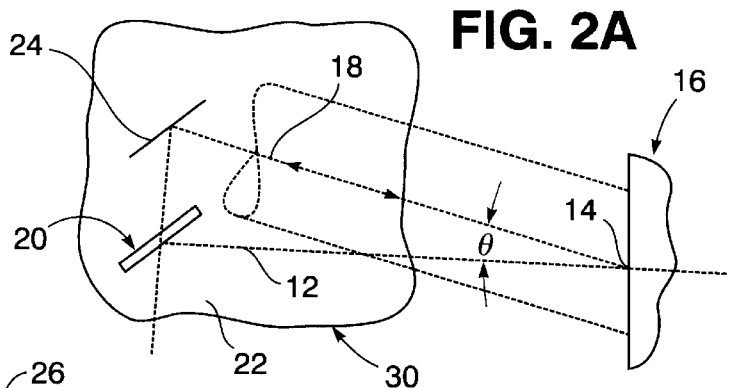
FIGS. 2A and 2B are schematic top and front views depicting certain geometric relationships associated with the arrangement depicted in FIG. 1.
Figure 2B:
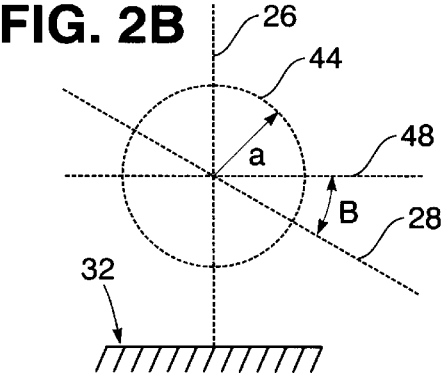

The geometry of the antenna and scattering plane arrangement corresponding to that of FIG. 1 is shown in FIGS. 2A and 2B with respect to the focus location 14 in the radiation targeted material 16. As diagrammed in FIG. 2A, the scattering plane 22 corresponding to paths 12 and 18 is depicted for both the position of the antenna 10 focussed along the path 12, and the other incidence position to which it is displaced along the translation path 28. The front view of FIG. 2B shows the antenna 10 positioned on the scattering plane 22 at an azimuthal angle (β) to horizontal axis 46. Based on the arrangement depicted in FIGS. 1, 2A and 2B, measurements of microwave radiation is utilized to identify and evaluate defects or flaws in the target 16 in accordance with different embodiments, including the embodiment disclosed in the aforementioned prior copending parent application.

Figure 3:
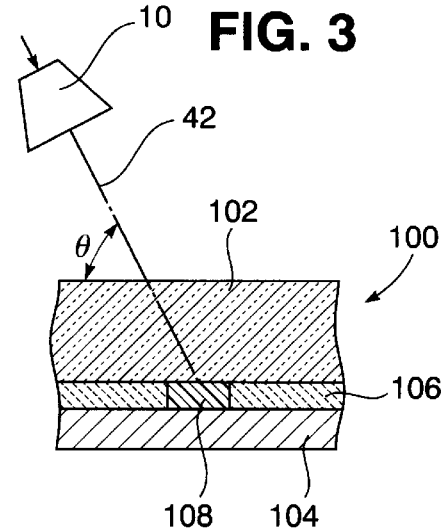
FIG. 3 is a partial section view of one type of radiation targeted structure having a thin internal glue bonding layer to which the defect detection and evaluation technique of the present invention is applied.
Figure 4:
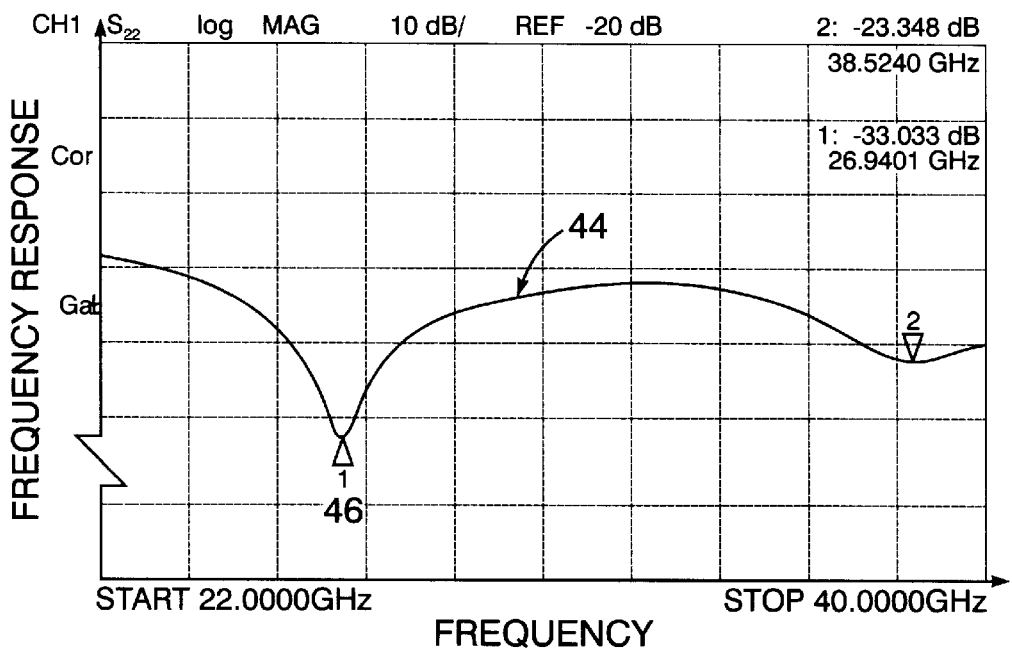
FIGS. 4, 5 and 6 are graphical plots of radiation measurement data associated with the defect detection and evaluation technique.
Figure 5:
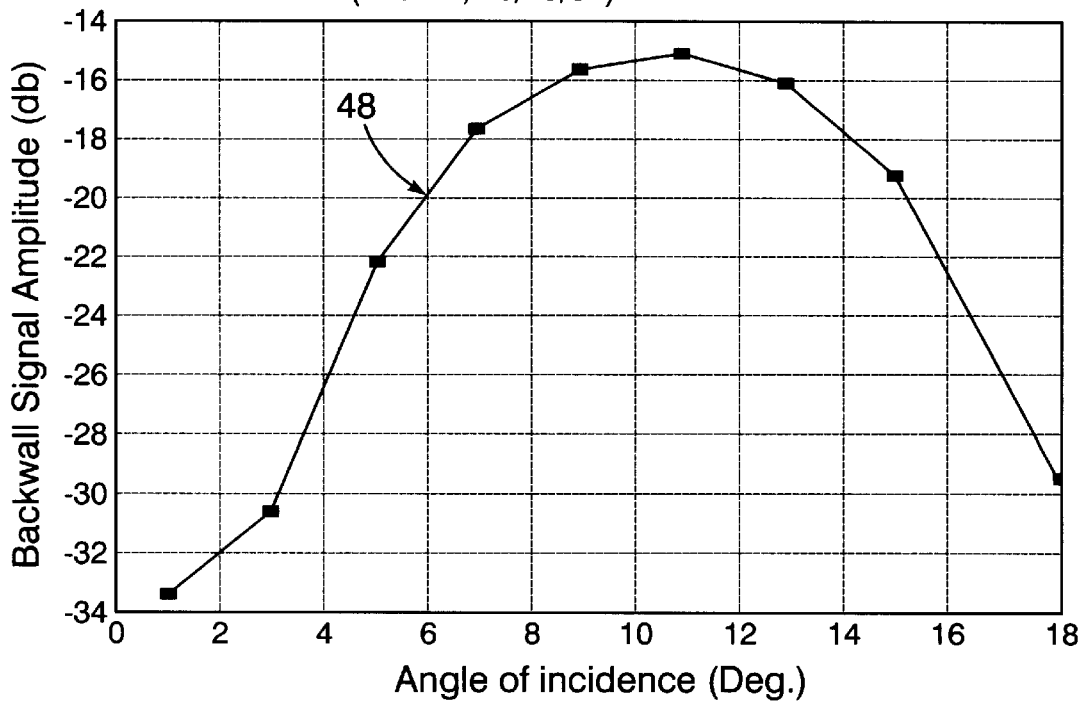
Figure 6:
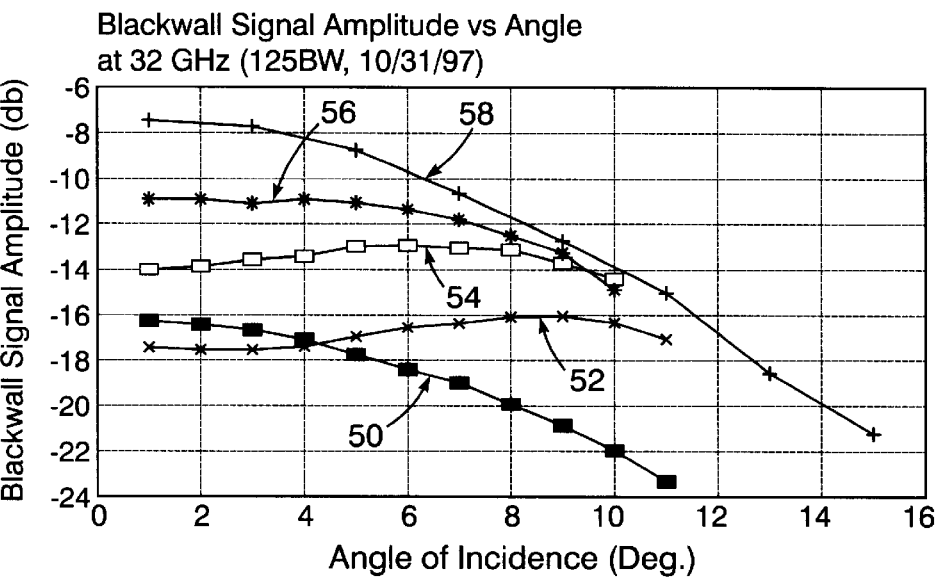

FIG. 3 illustrates a radiation targeted structure 100 subject to microwave radiation transmitted and reflected along an incidence path 42 for detection, location and sizing of interface defects near an internal thin layer 106 in accordance with one embodiment of the present invention. The structure 100 includes a rigid foam slab 102 bonded to a composite plate 104 by the thin layer 106 formed of interface bonding glue having a hole 108 therein as the simulated interface defect. Based on radiation measurements graphically depicted in FIG. 4, the frequency response varied along the ordinate for normal incidence is reflected by curve 44 indicating a typical resonance and anti-resonance type structure 100 with a dip at a frequency of 26.9401 GHz. As the angle (θ) of incidence of the radiation varied, the such frequency of the dip at point 46 on curve 44 shifted to higher frequencies. As a consequence, the radiation signal amplitude along the ordinate at this frequency shown in FIG. 5 for the graphical plot 48, reflects a sharp increase as the angle of incredence (θ) increases. In the absence of any defect, the systematic shift in frequency response does not occur. Instead, there is an overall decrease in signal amplitude for all frequencies as the angle of incidence increases. FIG. 6 graphically depicts the variations in signal amplitude of the measured radiation vs angle of incidence (θ) for targeted multi-layered type structures 100 having different void sizes. Curve 50 reflects no defect in the glue layer 106. Curves 52, 54 and 56 respectively reflect voids 108 having dimensions of 0.5"×0.06", 0.75"×0.06" and 1"×0.06". Curve 58 reflects a void 108 forming a complete airgap. It is apparent from the graphical plots 50, 52, 54, 56 and 58 in FIG. 6 that the frequency selected measurement at an angle of incidence (θ) between 8 and 10 degrees along the abscissa provides for defect detection within a signal amplitude range of 8 db along the ordinate. Thus, such graphically depicted data indicates that by recording only oblique incidence angle reflections, a defect is present when a certain signal amplitude value is exceeded for a small oblique incidence angle (θ) so as to discriminate against effects of target surface conditions. Also at oblique incidence, reflections unrelated to the defect and its immediate surroundings do not reach the antenna 10 so to reduce the need for Fourier transformation and time gating.

FIGS. 7 and 8 relate to other embodiments of the invention through which defects located at the interfaces between two materials are detected and evaluated and wherein at least one of such materials is non-metallic. As shown in FIG. 7A, a single antenna 10 is adjustably positioned and orientated for emission of probing microwave radiation at an incidence angle (θ) to the surface 78 of a slab 74 of non-metallic material having a metallic backing 76 to form a planar interface 80 underlying the surface 78. The radiation emission beam thus enters the surface 78 of slab 74 along the adjustably angled oblique incidence path 82 and is propagated through the non-metallic slab for reflection from the interface 80 and a 90 degree corner interface segment 84 at which slab 74 terminates. The reflected radiation accordingly emerges from surface 78 of slab 74 in spaced relation to the incidence path 82 along a reflective radiation path 86 for reception by the same antenna 10, as shown in FIG. 7A. Where the terminal end of the non-metallic slab 74 is remote from the incidence path 82, the antenna 10 is angularly adjusted relative to the interface 80 for travel of the microwave radiation through slab 74 as shown in FIG. 7B so as to provide for emergence of the reflected radiation along path 86 without repositioning of antenna 10 for recognition of reflected radiation.

Figure 7A:
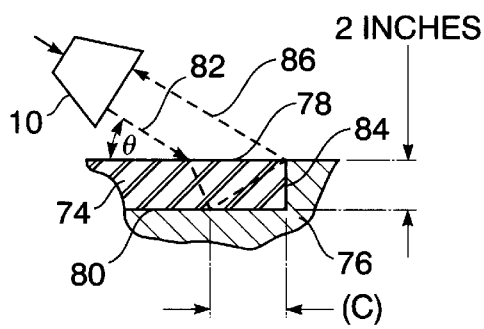
FIGS. 7A, 7B, 7C and 7D are partial section views illustrating different structures being probed by radiation for detection of defects.
Figure 7B:
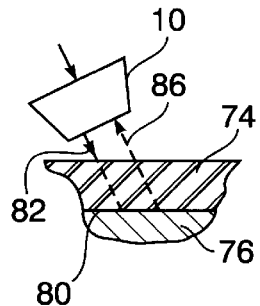
Figure 7C:
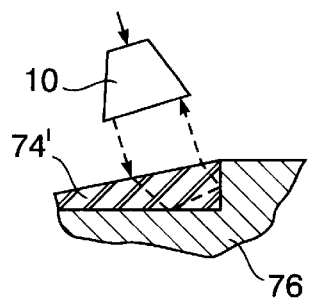
Figure 7D:
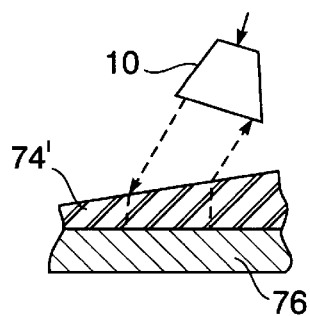

Travel of radiation from antenna 10 through a wedge-shaped slab 74' is shown in FIGS. 7C and 7D respectively corresponding to the slab arrangements shown in FIGS. 7A and 7B involving angular orientation and repositioning of the same antenna 10 for emission and reception of the microwave radiation from the boundaries of the interfaced slab 74' and metallic backing 76. The angular adjustment of the antenna 10 and repositioning thereof, as well as the supply of probing radiation for emission from the antenna is effected by electronic processing control through a reflectometer control system 37 and analyzer 34, as diagrammed in FIG. 1. A simplified system involves an arrangement as diagrammed in FIG. 8 for detection and evaluation of interface defects between the material layers depicted in FIGS. 7A, 7B, 7C and 7D.

In regard to defects located at the boundaries between two materials having a right angle geometry as shown in FIGS. 7A and 7C, the detection technique involving use of the single antenna 10 is particularly simplified since data collection at multiple frequencies or use of Fourier transform into the time domain for signal separation is not needed. Two factors for implementation of the defect detection technique are however important. One is selection of the incidence angle (θ) influenced by dielectric properties of the materials. Such incidence angle is dependent on the distance (c) as depicted in FIG. 7A, having its largest allowed value when the incidence angle reaches 90°. For materials having a dielectric constant between 2 and 3, incidence angles between 45° and 35° are used as a compromise between reduced specular reflection and adequate material penetration, where the height of the vertical segment in the 90° reflector was 2 inches as denoted in FIG. 7A.

With reference now to FIG. 8, microwave radiation is fed from a source 88 to a hybrid coupler 90 for transmission through a signal circulator 92 to the antenna 10 for both measured emission therefrom of transmitted radiation and measured reception of reflected radiation. A reflected radiation signal is accordingly fed from the signal circulator to a mixer system 94 from which an output signal is obtained for defect evaluation by evaluator 96. Part of the output of signal mixer system 94 is also fed to the antenna adjuster 40 through which the antenna 10 is angularly orientated and positioned so as to meet the requirements for defect evaluation at the interface boundary locations specified with respect to FIGS. 7A–7D. Electronic processing of transmitted radiation measurement signals and reflected radiation measurement signals by the mixer system 94 enables a signal adjuster 98 in the form of a phase controller or frequency controller to receive the output of mixer system 94 so as to provide a feedback thereto and a control input to the mixer system 94 in order to detect components of the reflected radiation in different phase relationships to the transmitted radiation, thereby maintaining a predetermined signal parameter such as a maximum signal amplitude or a selected signal frequency in response to the reflected radiation signal output fed to the evaluator 96. Continuous measurement of radiation reflection and detection of defects is thereby maintained. Furthermore, through the adjuster 40 the condition of maximum signal amplitude or selected signal frequency is made to coincide with proper orientation and positioning of the antenna 10 for reception of retroreflected radiation from the interface 80 being evaluated.

The foregoing described single antenna technique for non-destructive defect evaluation is applicable to structural arrangements such as an acoustic or thermal absorbing coating corresponding to non-metallic slab 74 on flat or wedged-shaped backings such as metallic hulls of Naval vessels, without prior knowledge of material thickness or electrical properties. The electronic feedback from the signal adjuster 98 diminishes potential effects of misalignment variations during reflectometric scanning of interface surfaces for mapping defect locations. Signal amplitude maximization or maintenance of selected frequency response as hereinbefore referred to enables maintenance of the correct angle of incidence (θ) of the antenna 10 during emission of probing radiation for the occurrence of retroreflection and to compensate for small material and geometric variations.

The operating frequencies for the system 37 diagrammed in FIG. 8, are selected near the midfrequency between peak and valley values in the frequency domain, based on the natural resonance and anti-resonance of the target structure dependent on its thickness and material properties. Because of interference between the signal originating from the defect and the resonating response of its nearby structure, the oblique incidence signal is observed to be larger when a defect is present as compared to the absence of a defect at frequencies midway between natural resonance nodes and antinodes of the target structure. At an oblique incidence angle (θ) of 10 degrees for example, the adverse effects of material surface roughness is also substantially diminished.

Obviously, other modifications and variations of the present invention may be possible in light of the foregoing teachings. It is therefore to be understood that within the scope of the appended claims the invention may be practiced otherwise than as specifically described.

What is claimed is:

1. A system for detection of flaws in a structure by probing a targeted portion thereof with microwave radiation from which readings are obtained by signal measurement of radiation reflections from the targeted portion of the structure, the improvement residing in the steps of: focussing travel of the probing radiation along a single oblique incidence path relative to the targeted portion of the structure; utilizing said readings on the signal measurement of the radiation reflections derived from said oblique incidence path to indicate said detection of the flaws; and measuring signal parameter differences between the radiation and the radiation reflections in order to signify maximized signal amplitude to enable said detection of the flaws.

2. The system as defined in claim 1, wherein said targeted portion of the structure resides in a bonding interface with a thin internal layer of the structure.

3. The system as defined in claim 2 wherein the probing radiation along said oblique incidence path is emitted at different frequencies selected for said detection of the flaws by comparison of the readings.

4. The system as defined in claim 1 wherein the targeted portion of the structure is interfacing between a non-metallic coating and a metallic backing.

5. The system as defined in claim 4 wherein the probing radiation is emitted from a single antenna angularly adjusted between positions to establish said oblique incidence path focussed on the targeted portion of the structure.

6. The system as defined in claim 1 wherein the probing radiation is emitted from a single antenna angularly adjusted between positions to establish said oblique incidence path focussed on the targeted portion of the structure.

7. A system for detection of flaws in a structure by probing a targeted portion thereof with microwave radiation from which readings are obtained by signal measurement of radiation reflections from the targeted portion of the structure, the improvement residing in the steps of: emitting the probing radiation from a single antenna angularly adjusted between positions to establish an oblique incidence path; focusing travel of the probing radiation only along said oblige incidence path relative to the targeted portion of the structure; utilizing said readings on the signal measurement of the radiation reflections derived from said oblique incidence path to indicate said detection of the flaws; and measuring signal parameter differences between the radiation emitted from the antenna and the radiation reflections in order to signify the positions of the antenna at which the signal amplitude is maximized to enable said detection of the flaws.

8. The system as defined in claim 7, wherein said structure includes interfacing layers having right angle boundaries, one of said layers being made of metallic material; the flaws being located adjacent to said right angle boundaries.

* * * * *